(12) United States Patent
Helton et al.

(10) Patent No.: US 9,440,893 B2
(45) Date of Patent: Sep. 13, 2016

(54) PRODUCTION OF PARA-XYLENE

(71) Applicant: ExxonMobil Chemical Patents Inc., Baytown, TX (US)

(72) Inventors: Terry E. Helton, Bethlehem, PA (US); Robert G. Tinger, Friendswood, TX (US); Lu Han, Herndon, VA (US); Andrea P. Wight, Huffman, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 178 days.

(21) Appl. No.: 14/153,399

(22) Filed: Jan. 13, 2014

(65) Prior Publication Data
US 2014/0213840 A1    Jul. 31, 2014

Related U.S. Application Data

(60) Provisional application No. 61/759,087, filed on Jan. 31, 2013.

(51) Int. Cl.
*C07C 2/66* (2006.01)
*C07C 1/00* (2006.01)
*C07C 2/86* (2006.01)

(52) U.S. Cl.
CPC ............... *C07C 2/862* (2013.01); *C07C 2/864* (2013.01); *C07C 2521/16* (2013.01); *C07C 2529/40* (2013.01)

(58) Field of Classification Search
CPC .................................. C07C 2/66; C07C 1/00
USPC .................................................. 585/467, 469
See application file for complete search history.

(56) References Cited

U.S. PATENT DOCUMENTS

| | | |
|---|---|---|
| 6,423,879 B1 | 7/2002 | Brown et al. |
| 6,504,072 B1 | 1/2003 | Brown et al. |
| 7,399,727 B2 | 7/2008 | Ghosh et al. |
| 2004/0097769 A1 | 5/2004 | Ou et al. |
| 2005/0036295 A1 | 2/2005 | Beeckman et al. |
| 2009/0000988 A1 | 1/2009 | Brown et al. |
| 2011/0092755 A1 | 4/2011 | Lattner et al. |

OTHER PUBLICATIONS

Yashima et al., "*Alkylation on Synthetic Zeolites*," Journal of Catalysis vol. 16, Issue 3, Mar. 1970, pp. 273-280.

*Primary Examiner* — Thuan D Dang

(57) ABSTRACT

In a process for producing para-xylene, benzene and/or toluene is alkylated with methanol in the presence of a catalyst under conditions including a temperature of at least 500° C. and an $H_2O$ partial pressure of at least 12 psia (83 kPaa). The catalyst comprises from 5 to 15 wt % ZSM-5, phosphorus or a compound thereof and a binder and has been steamed at a temperature of at least 900° C. The steamed catalyst has no more than two peaks in the $^{31}P$ MAS NMR spectrum in the range of 0 to −50 ppm.

9 Claims, 1 Drawing Sheet

US 9,440,893 B2

PRODUCTION OF PARA-XYLENE

CROSS REFERENCE TO RELATED APPLICATIONS

This application claims the priority to and the benefit of U.S. Provisional Application No. 61/759,087, filed on Jan. 31, 2013, the disclosure of which is incorporated herein by reference in its entirety.

FIELD

This invention relates to a process for producing para-xylene by the alkylation of benzene and/or toluene with methanol.

BACKGROUND

Of the xylene isomers, para-xylene is of particular value since it is useful in the manufacture of terephthalic acid which is an intermediate in the manufacture of synthetic fibers. Equilibrium mixtures of xylene isomers either alone or in further admixture with ethylbenzene generally contain only about 22-24 wt % para-xylene and separation of para-xylene from such mixtures typically requires superfractionation and multistage refrigeration steps. Such processes involve high operational costs and result in only limited yields. There is therefore a continuing need to provide processes for producing xylenes which are highly selective for para-isomer.

One known method for producing xylenes involves the alkylation of toluene with methanol over a solid acid catalyst. Thus the alkylation of toluene with methanol over cation-exchanged zeolite Y has been described by Yashima et al. in the Journal of Catalysis 16, 273-280 (1970). These workers reported selective production of para-xylene over the approximate temperature range of 200 to 275° C., with the maximum yield of para-xylene in the mixture of xylenes, i.e., about 50% of the xylene product mixture, being observed at 225° C. Higher temperatures were reported to result in an increase in the yield of meta-xylene and a decrease in production of para and ortho-xylenes.

More recently, selectivities to para-xylene in excess of 90 wt % (based on total $C_8$ aromatic product) have been reported by reacting toluene with methanol in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa). The porous crystalline material is preferably a medium-pore zeolite, particularly ZSM-5, which has been severely steamed at a temperature of at least 950° C. in the presence of at least one oxide modifier, preferably including phosphorus, to control reduction of the micropore volume of the material during the steaming step. See U.S. Pat. Nos. 6,423,879 and 6,504,072.

In contrast, U.S. Pat. No. 7,399,727 reports that improved selectivity in the methylation of toluene to para-xylene can be achieved through the use of a catalyst comprising a phosphorus-containing ZSM-5-type zeolite having a silica/alumina molar ratio of at least 200, a phosphorus content of at least 8% by weight of zeolite and multiple phosphorus species exhibited by multiple $^{31}P$ MAS NMR peaks with maxima at from about 0 to about −50 ppm. The phosphorus-containing ZSM-5 may be used without steaming or may be steamed at low or mild temperatures, such as from about 150° C. to about 350° C. In addition, the phosphorus-containing ZSM-5 may be used with or without a binder.

According to the present invention, it has now been found that certain severely steamed, phosphorus-containing, bound ZSM-5 catalysts show a unique combination of selectivity and stability when used in the methylation of toluene and/or benzene to para-xylene at high steam partial pressures. Since water is an inevitable by-product of the methylation process, the ability of the catalyst to retain its selectivity over long periods of time at high steam partial pressures represents a significant advantage over existing processes.

SUMMARY

In one aspect, the invention resides in a process for producing para-xylene, the process comprising:
 (a) providing a catalyst comprising ZSM-5, phosphorus and a binder wherein the catalyst contains 5 to 15 wt % ZSM-5 and has been steamed at a temperature of at least 900° C., such that the steamed catalyst has a Diffusion Parameter for 2,2 dimethylbutane of about 0.1-15 $sec^{-1}$ when measured at a temperature of 120° C. and a 2,2 dimethylbutane pressure of 60 torr (8 kPa); and
 (b) alkylating benzene and/or toluene with an alkylating agent such as methanol and or dimethylether (DME) in the presence of said steamed catalyst under conditions including a temperature of at least 500° C. and an $H_2O$ partial pressure of at least 12 psia (83 kPaa).

In embodiments, the steamed catalyst has only one peak in the $^{31}P$ MAS NMR spectrum in the range of 0 to −50 ppm.

In embodiments, the catalyst in (a) comprises from 2 to less than 8 wt % of elemental phosphorus.

In embodiments, the catalyst in (a) contains from 8 to 10 wt % ZSM-5 and the ZSM-5 is an aluminosilicate having a silica/alumina molar ratio of at least 200.

In embodiments, the catalyst contains from 75 to 90 wt % binder and the binder comprises silica and/or a clay, such as kaolin.

In embodiments, the catalyst in (a) has been steamed at a temperature of at least 900° C. for between about 10 minutes and about 10.0 hours.

In embodiments, the conditions in (b) include an $H_2O$ partial pressure of at least 15 psia (103 kPaa).

In embodiments, the conditions in (b) also include a temperature between about 500 and 700° C., a pressure of between about 1 atmosphere and 1000 psig (100 and 7000 kPa), a weight hourly space velocity between about 0.5 and about 1000 and a molar ratio of toluene to methanol of at least about 0.2.

It is an object of the invention to provide an improved process for making paraxylene selectively, and a further object to provide a process for making paraxylene is selectively with a catalyst that has improved thermal stability.

These and other objects, features, and advantages of the present invention will become apparent in the following detailed description, drawings, specific embodiments, experiments, and accompanying claims.

DETAILED DESCRIPTION OF THE EMBODIMENTS

Figure 1A:
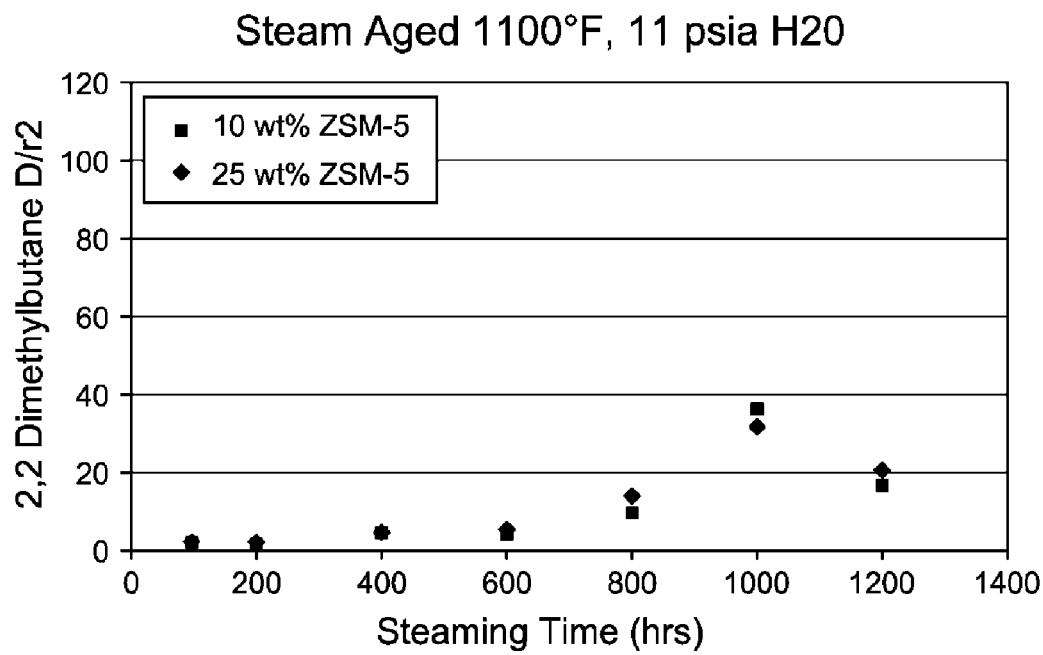
FIGS. 1(a) and 1(b) are graphs comparing 2,2 dimethyl butane diffusivity (D/r2) against steaming time for the catalysts of Example 1 (steamed at 985° C.) and Example 2 (steamed at 1060° C.) when subjected to the hydrothermal aging tests of Example 4 at a steam partial pressure of 11 psia and a steam partial pressure of 15.7 psia.

Described herein is a process for producing para-xylene by the catalytic alkylation of benzene and/or toluene with an alkylating agent such as methanol and/or dimethylether (DME) in the presence of a severely steamed catalyst comprising ZSM-5, phosphorus and a binder. In particular, it is found that, when the catalyst contains from 5 to 15 wt % ZSM-5, the catalyst exhibits a unique combination of hydrothermal stability, para-selectivity and activity when operated at high steam partial pressures in excess of at least 12 psia (83 kPaa), such as about 15 psia (about 104 kPaa) or higher.

The alkylation process employed herein can use any aromatic feedstock comprising toluene and/or benzene, although in general it is preferred that the aromatic feed contains at least 90 weight % (wt %), especially at least 99 wt %, of benzene, toluene or a mixture thereof. An aromatic feed containing at least 99 wt % toluene is particularly desirable. Similarly, although the composition of the methanol-containing feed is not critical, it is generally desirable to employ feeds containing at least 90 wt % especially at least 99 wt %, of methanol.

The catalyst employed in the alkylation process comprises ZSM-5 modified with phosphorus, normally in an oxide form, and combined with a binder.

Zeolite ZSM-5 and the conventional preparation thereof are described in U.S. Pat. No. 3,702,886, the entire disclosure which is incorporated herein by reference. The ZSM-5 employed in the present process is typically an aluminosilicate or silicate having a silica ($SiO_2$) to alumina ($Al_2O_3$) molar ratio of at least 200, as measured prior to any steaming of the catalyst to adjust its diffusivity.

Incorporation of phosphorus modifier in the catalyst is conveniently achieved by the methods described in U.S. Pat. Nos. 4,356,338, 5,110,776, 5,231,064 and 5,348,643, is the entire disclosures of which are incorporated herein by reference. Treatment with phosphorus-containing compounds can readily be accomplished by contacting the ZSM-5, either alone or in combination with a binder material, with a solution of an appropriate phosphorus compound, followed by drying and calcining to convert the phosphorus to its oxide form. Contact with the phosphorus-containing compound is generally conducted at a temperature between about 25° C. and about 125° C. for a time between about 15 minutes and about 20 hours. The concentration of the phosphorus in the contact mixture may be between about 0.01 and about 30 wt %.

After preparation of the phosphorus-containing compound, the catalyst may be dried and calcined to convert the phosphorus to an oxide form. Calcination can be carried out in an inert atmosphere or in the presence of oxygen, for example, in air at a temperature between about 150 to 850° C., such as from 300 to 650° C., or about 540 to 810° C., for at least 30 minutes (mins), such as from 45 to 90 mins or from 30 to 60 mins.

Representative phosphorus-containing compounds which may be used to incorporate a phosphorus oxide modifier into the catalyst have been previously disclosed in U.S. Pat. No. 6,504,072.

The phosphorus oxide modifier is generally present in the catalyst in an amount such that the catalyst contains from 1 to 10 wt %, for example from 2 to less than 8 wt %, such as from 2 to 6 wt %, of phosphorus, based on elemental phosphorus.

In a preferred embodiment, the phosphorus source, such as phosphoric acid, is added to a slurry of ZSM-5 in deionized water. Then clay, for example a kaolin clay such as Thiele RC-32, is then added to the slurry of ZSM-5 and phosphorus compound. The spray dried product from this step is then calcined, preferably in air and at a nominal temperature of between about 540-810° C., prior to steaming.

The catalyst employed in the present process preferably includes a binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials.

Naturally occurring clays which can be utilized in the present catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. It will be recognized that the specific clay used and treatment thereof will affect performance to some extent, and the determination of the most appropriate clay (or binder more generally) is within the skill of the ordinary artisan in possession of the present disclosure to determine by routine experimentation.

In addition to the foregoing materials, the ZSM-5 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

Generally, the catalyst will contain from 75 to 90 wt % of the binder.

The catalyst employed in the present process is preferably steamed such that the steamed catalyst has a Diffusion Parameter for 2,2 dimethylbutane of about 0.1-15 $sec^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient ($cm^2/sec$) and r is the crystal radius (cm). The diffusion parameter can be derived from sorption measurements provided the assumption is made that the plane sheet model describes the diffusion process. Thus for a given sorbate loading Q, the value $Q/Q_{eq}$, where $Q_{eq}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The steaming of the catalysts is arranged so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired diffusivity and reduction in the micropore volume of the porous crystalline material can be effected by heating the material in the presence of steam at a temperature of at least about 900° C., preferably about 950 to about 1075° C., and most preferably about 1000 to about 1050° C., and for time period of from about 10 minutes to about 10 hours, preferably from 30 minutes to 5 hours, such as 30 minutes to 2 hours. Other preferred temperature and temperature ranges include any of the lower temperatures and/or times listed in this paragraph to any of the higher temperatures and/or times listed herein, e.g., from about 900 to 1050° C. for about 10 minutes to 2 hours, and so on.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

A particularly preferred system for the alkylation process of the invention is described in U.S. patent application Ser. No. 13/557,605. However, the present invention is generally applicable to fixed bed, moving bed, or fluid bed reactors.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig is (between about 170 and about 1480 kPa); (c) moles toluene/moles methanol (in the reactor charge) of at least about 0.2, such as from about 0.2 to about 20; and (d) a weight hourly space velocity ("WHSV") for total hydrocarbon feed to the reactor(s) of about 0.2 to about 1000, such as about 0.5 to about 500 for the aromatic reactant, and about 0.01 to about 100 for the combined methanol reagent stage flows, based on total catalyst in the reactor(s).

In addition to producing para-xylene and other xylene isomers, the present process produces water vapor which, at the high temperatures employed in the process, can lead to rapid aging of the catalyst. Notwithstanding that water is produced in the reaction, water is also advantageously and preferably added to the reaction, such as in one or more of the aromatic feed(s) and/or alkylating agent feed(s). Addition of water in this manner has been found to increase alkylation agent conversion, decrease side reactions, and also decrease coking in furnace(s) used to heat feedstreams to the reactor.

As is shown in the following Examples and the accompanying figures, the present catalyst exhibits improved hydrothermal stability and para-selectivity as compared with catalysts with ZSM-5 loadings in excess of 15 wt % even when operated at steam partial pressures in excess of at least 12 psia (83 kPaa). This allows the methylation process to be conducted without expensive measures being taken to reduce the steam partial pressure to be reduced in the methylation reactor. In addition, provided the ZSM-5 content is maintained at or above 5 wt %, the advantageous hydrothermal stability and para-selectivity properties can be achieved without undue loss in the activity of the catalyst.

In the examples below, the steam partial pressure is taken as an average across the total reaction zone, as measured by thermocouples at the inlet and outlet of the reactor. The maximum stream partial pressure will depend on total reactor pressure, which is advantageously between about 1 atmosphere and 1000 psig (100 and 7000 kPa).

Example 1

Three samples of a catalyst containing 25 wt % ZSM-5, nominally 4 wt % phosphorus, and the balance clay, made by the preferred process set forth above, wherein clay binder is added after the ZSM-5 and phosphorus source are slurried together, were steamed in a rotary calciner in 14.7 psia, and then steamed in 100% steam for 45 minutes at 1060° C.

Example 2

Three samples of a catalyst nominally containing 10 wt % ZSM-5, nominally 4 is wt % phosphorus, and the balance clay, made in the same manner as in Example 1, were steamed in a rotary calciner in 14.7 psia, and then steamed in 100% steam for 45 minutes at 985° C.

Figure 1B:
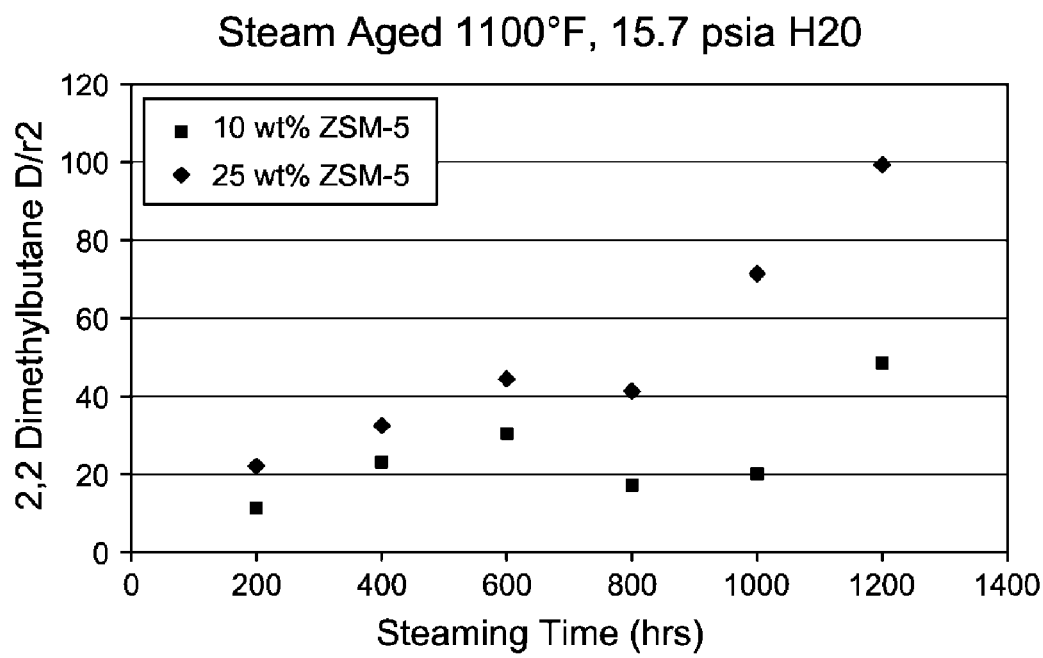

Two 50-day hydrothermal aging studies were conducted on the catalyst of Example 1 (25 wt % ZSM-5, nominally 4 wt % P), and on the catalyst of Example 2 (10 wt % ZSM-5, nominally 4 wt % P). In the first study the catalysts were heated at 1100° F. (593° C.) in 11 psia (76 kPaa) steam, whereas in the second study the temperature remained the same but the steam partial pressure was increased to 15.7 psia (108 kPaa). The hydrothermal stability was measured in terms of the 2,2-dimethyl butane diffusivity (D/r2) of the catalyst. The results are shown in FIGS. 1(a) and 1(b) and clearly show that, whereas the long term stability of the catalysts are very similar when heated in 11 psia steam, the 10 wt % ZSM-5 catalyst is clearly more hydrothermally stable at 15.7 psia steam partial pressure as compared to the 25 wt % ZSM-5 catalyst.

While the present invention has been described and illustrated by reference to particular embodiments, those of ordinary skill in the art will appreciate that the invention lends itself to variations not necessarily illustrated herein.

The invention claimed is:

1. A process for producing para-xylene, the process comprising:
(a) providing a catalyst comprising ZSM-5, phosphorus or a compound thereof and a clay binder, wherein the catalyst contains from 5 to 15 wt % ZSM-5 and has been steamed at a temperature of at least 900° C., wherein said steamed catalyst has a Diffusion Parameter for 2,2 dimethylbutane of about 0.1-15 sec$^{-1}$ when measured at a temperature of 120° C. and a 2,2 dimethylbutane pressure of 60 torr (8 kPa); and (b) alkylating benzene and/or toluene with an alkylating agent selected from methanol, dimethyl ether, and mixtures thereof to produce para-xylene and water vapor as a by-product, in the presence of said steamed catalyst under conditions including a temperature of at least 500° C. and an H$_2$O partial pressure of at least 4-15 psia (about 104 kPaa), wherein additional steaming of the catalyst occurs during the alkylation reaction and the Diffusion Parameter for 2,2 dimethylbutane of the catalyst does not exceed about 35 sec$^{-1}$ during the reaction.

2. The process of claim 1, wherein the catalyst in (a) comprises from 2 to less than 8 wt % of elemental phosphorus.

3. The process of claim 1, wherein the ZSM-5 is an aluminosilicate having a silica/alumina molar ratio of at least 200.

4. The process of claim 1, wherein the catalyst contains from 8 to 10 wt % ZSM-5.

5. The process of claim 1, wherein the catalyst contains from 75 to 90 wt % binder.

6. The process of claim 1, wherein the catalyst in (a) has been steamed at a temperature of at least 900° C. for between about 10 minutes and about 1.5 hours.

7. The process of claim 1, wherein said conditions in (b) also include a temperature between about 500 and 700° C., a total reactor pressure of between about 1 atmosphere and 1000 psig (100 and 7000 kPa), a weight hourly space velocity between about 0.5 and about 1000 and a molar ratio of toluene to methanol of at least about 0.2.

8. The process of claim 1, wherein the upper limit of H$_2$O partial pressure is less than 1000 psig (7000 kPa).

9. The process of claim 1, wherein the silica/alumina molar ratio of the catalyst is less than 1,000.

\* \* \* \* \*

UNITED STATES PATENT AND TRADEMARK OFFICE
CERTIFICATE OF CORRECTION

PATENT NO. : 9,440,893 B2  
APPLICATION NO. : 14/153399  
DATED : September 13, 2016  
INVENTOR(S) : Helton et al.

It is certified that error appears in the above-identified patent and that said Letters Patent is hereby corrected as shown below:

In the Claims

Column 7, Line 13 Claim 1 change "4-15 psia" to --15 psia--.

Signed and Sealed this
Fourteenth Day of March, 2017

Michelle K. Lee
*Director of the United States Patent and Trademark Office*